Figures 1, 3:
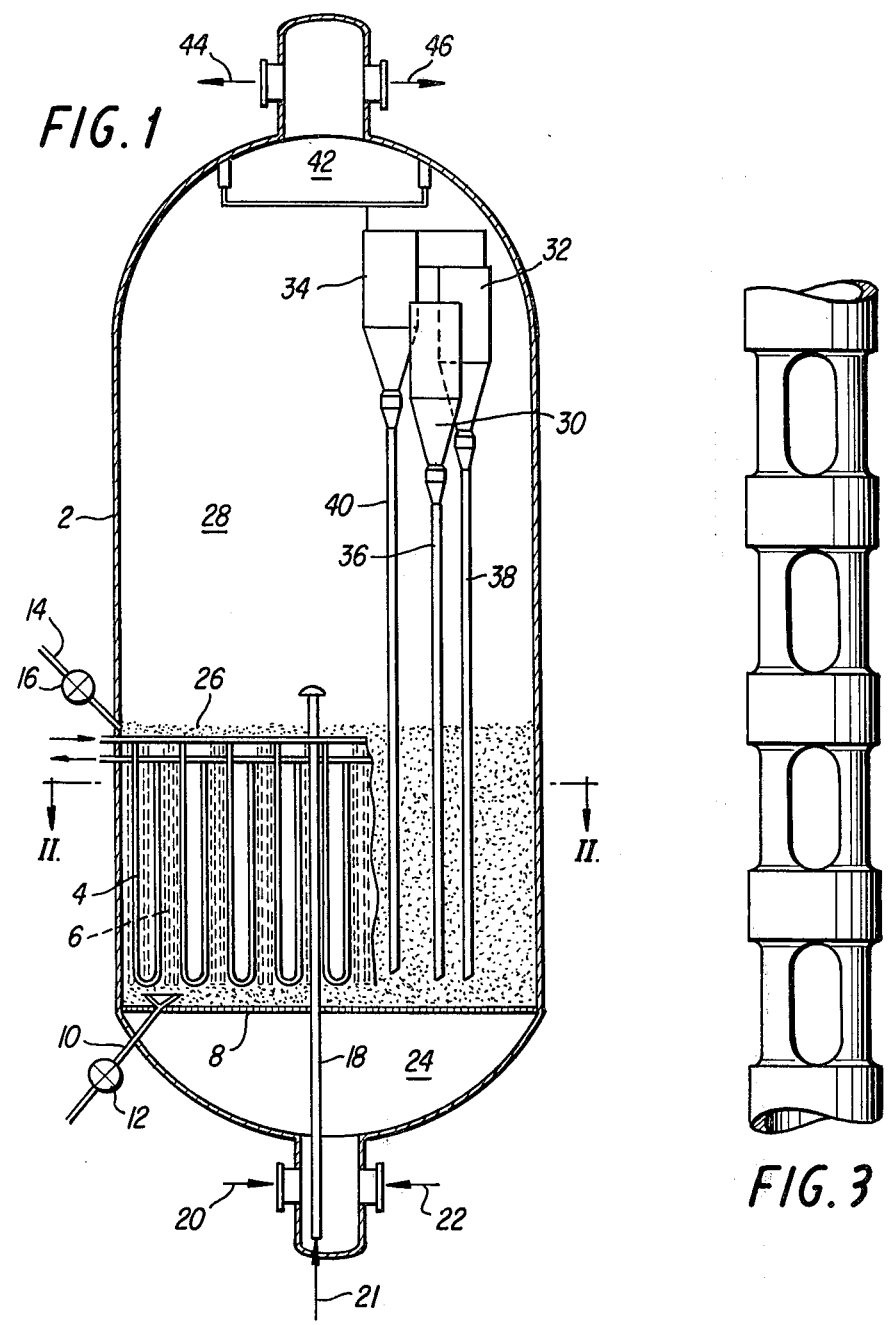
Figure 2:
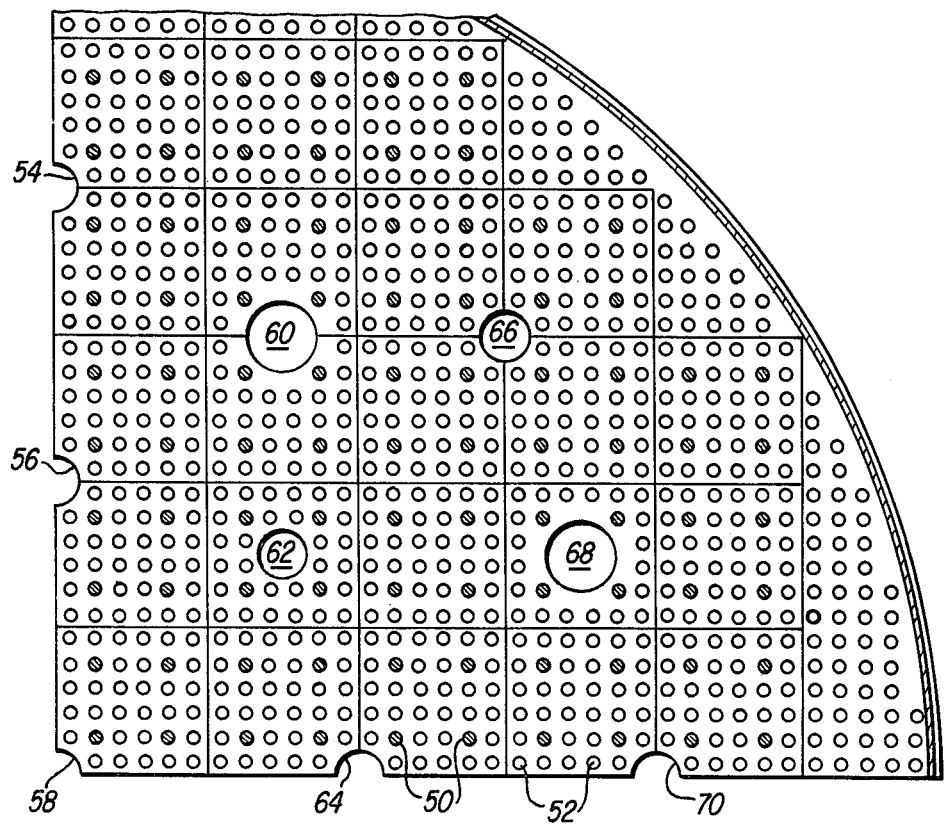

United States Patent [19]

Daviduk et al.

[11] 4,423,274

[45] * Dec. 27, 1983

[54] METHOD FOR CONVERTING ALCOHOLS TO HYDROCARBONS

[75] Inventors: Nicholas Daviduk, Pennington; James H. Haddad, Princeton Junction, both of N.J.

[73] Assignee: Mobil Oil Corporation, New York, N.Y.

[*] Notice: The portion of the term of this patent subsequent to Jul. 6, 1999, has been disclaimed.

[21] Appl. No.: 368,549

[22] Filed: Apr. 15, 1982

Related U.S. Application Data

[60] Continuation-in-part of Ser. No. 193,675, Oct. 3, 1980, Pat. No. 4,338,475, which is a division of Ser. No. 89,705, Oct. 30, 1979, Pat. No. 4,251,484.

[51] Int. Cl.$^3$ .......................... C07C 1/20; C07C 1/24
[52] U.S. Cl. .......................................................... 585/640
[58] Field of Search ................................................ 585/640

[56] References Cited

U.S. PATENT DOCUMENTS

| | | | |
|---|---|---|---|
| 3,928,483 | 12/1975 | Chang et al. | 260/668 R |
| 3,931,349 | 1/1976 | Kuo | 260/668 R |
| 3,969,426 | 7/1976 | Owen et al. | 260/668 R |
| 3,998,899 | 12/1976 | Daviduk et al. | 260/668 R |
| 4,013,732 | 3/1977 | Chang et al. | 260/668 R |
| 4,035,430 | 7/1977 | Dwyer et al. | 260/668 R |
| 4,044,061 | 8/1977 | Chang et al. | 260/668 R |
| 4,046,825 | 9/1977 | Owen et al. | 260/668 R |
| 4,052,479 | 10/1977 | Chang et al. | 260/682 |
| 4,058,576 | 11/1977 | Chang et al. | 260/673 |
| 4,062,905 | 12/1977 | Chang et al. | 260/682 |
| 4,071,573 | 1/1978 | Owen et al. | 260/668 R |
| 4,076,761 | 2/1978 | Chang et al. | 260/668 R |
| 4,079,095 | 3/1978 | Givens et al. | 585/640 |
| 4,083,888 | 4/1978 | Caesar et al. | 585/640 |
| 4,083,889 | 4/1978 | Caesar et al. | 585/640 |
| 4,118,431 | 10/1978 | Chen | 260/668 R |
| 4,138,440 | 2/1979 | Chang et al. | 260/668 R |
| 4,247,731 | 1/1981 | Wunder et al. | 585/640 |
| 4,296,266 | 10/1981 | Wunder et al. | 585/640 |
| 4,306,106 | 12/1981 | Kerr et al. | 585/640 |
| 4,338,475 | 7/1982 | Daviduk et al. | 585/640 X |

*Primary Examiner*—Paul F. Shaver
*Attorney, Agent, or Firm*—Charles A. Huggett; Michael G. Gilman; Stanislaus Aksman

[57] ABSTRACT

Apparatus and method of its utilization for controlling exothermic reactions such as the conversion of methanol to either olefin-enriched or gasoline boiling range hydrocarbons are disclosed. More particularly, the arrangement of fluid catalyst bed apparatus can be employed under varying reaction conditions in order to adjust contact between vaporous reactant and fluidized catalyst so as to maximize production as desired of either gasoline boiling range products or olefinic products useful as chemical feedstocks.

9 Claims, 3 Drawing Figures

METHOD FOR CONVERTING ALCOHOLS TO HYDROCARBONS

CROSS-REFERENCE TO RELATED APPLICATIONS

This application is a continuation-in-part of the co-pending application of Nicholas Daviduk and James H. Haddad, having Ser. No. 193,675, filed Oct. 3, 1980 now U.S. Pat. No. 4,338,475, which in turn is a divisional of the application of Nicholas Daviduk and James H. Haddad, having Ser. No. 089,705, filed Oct. 30, 1979, now U.S. Pat. No. 4,251,484.

BACKGROUND OF THE INVENTION

The application of fluidized catalyst techniques for effecting chemical reactions embodying the distribution of heat and/or the disposal of undesired reaction heat has long been accepted as a major processing tool of the petroleum and chemical industry. For example, it has been proposed to use the fluidized catalyst technique in the exothermic reactions of Fischer-Tropsch synthesis, the known Oxo process as well as others for the disposal of generated heat. In the fluid catalytic cracking of hydrocarbons, the fluid catalyst conveys heat generated in the catalyst regeneration zone to the hydrocarbon conversion zone wherein the conveyed heat is given up by converting hydrocarbons admixed therewith to form more desirable hydrocarbon products such as gasoline. In these various fluidized catalyst operations, disposal of the reaction heat has been accomplished by different techniques including the transfer of heat to cooling coils, and indirect heat exchange with fluidized catalyst particles or reactant feed streams and product streams.

The conversion of lower alcohols, such as methanol, to intermediate ether products followed by conversion of the ether product to one or a combination of products comprising olefins and/or aromatics has been the subject of several patents. Such patents include U.S. Pat. Nos. 3,928,483; 3,931,349; 3,969,426; 3,998,899; 4,013,732; 4,035,430; 4,044,061; 4,046,825; 4,052,479; 4,058,576; 4,062,905; 4,071,573; 4,076,761; 4,118,431 and 4,138,440. These patents and others have been considered in the preparation of this application.

Some other patents given consideration include U.S. Pat. Nos. 2,493,526; 2,571,380; 2,627,522; 2,920,940 and 3,151,944. These patents relate to fluidized catalyst bed systems in general.

SUMMARY OF THE INVENTION

One embodiment of this invention relates to an arrangement of apparatus and its method of utilization for effecting the conversion of lower alcohols such as methanol, ethanol, and propanol, ether derivatives thereof and mixtures of alcohols, ethers and other oxygenates in the presence of fluid catalyst particles of a special class of crystalline zeolites to form hydrocarbons enriched in gasoline boiling range hydrocarbons and characterized by the presence of olefinic and/or aromatic hydrocarbons. About 15%–25% of such a hydrocarbon product comprises olefins with the remainder of the hydrocarbon product primarily consisting of gasoline boiling range liquid hydrocarbons along with small quantities (about 5–12% by weight) of liquefied petroleum gas (LPG) material and light hydrocarbon gases.

Another embodiment of the present invention relates to a separate method for utilizing such apparatus to effect the conversion of these same lower alcohols, ether derivatives, other oxygenates and mixtures thereof in the presence of the same fluid particles of zeolite catalyst to form olefin-enriched hydrocarbon products suitable as petrochemical feedstocks. Products of this type generally comprise from about 25% to 67%, more generally from about 25% to 45% of $C_2^+$ olefins with a prepondence of such olefins comprising $C_2$–$C_5$ olefins. The remainder of such an "olefin-enriched" hydrocarbon product consists primarily of gasoline boiling range hydrocarbons, liquefied petroleum gas (LPG) material and light hydrocarbon gases.

More particularly, the present invention is directed to an arrangement of apparatus for effecting the conversion of a methanol-containing charge in the presence of fluid catalyst particles comprising a special zeolite characterized as providing a pore opening of at least 5 Angstroms, a silica/alumina ratio of at least 12 and a Constraint Index within the range of 1 to 12. The arrangement of apparatus comprises in combination a cylindrical reactor housing a generally upflowing fluidized relatively dense mass of catalyst particles initially contacted by vapor and/or liquid lower alcohols, ether derivatives thereof and related oxygenates or a mixture thereof. The charge may be methanol or other lower alcohols alone, or such alcohols in admixture with ethers such as dimethyl ether (DME) and related oxygenates including oxygenates of Fischer-Tropsch synthesis. The term "lower alcohols" is used herein to designate either purified lower alcohols or unpurified alcohols which have not been treated to remove impurities produced in the manufacturing process. For example, crude methanol, as known in the art, is methanol freshly produced in a methanol plant. Such crude methanol may contain a number of impurities, e.g. other alcohols such as ethanol, propanol, and butanol; oxygenates such as ketones, ethers and aldehydes; a substantially higher amount of water, e.g. up to 30% by weight, than is found in purified alcohol; and some gases such as CO, $CO_2$, $H_2$ and $CH_4$.

The reactor can be provided with a plurality of vertically arranged steam generation tubes in combination with juxtapositioned special gas bubble dispersing baffle tubes confined particularly within the most dense portion of the fluid mass of catalyst particles within the lower portion of the reactor. A catalyst regenerator is provided adjacent the reactor in combination with associated subsystems provided for preheating the methanol feed, reactor effluent cooling and recovery, a catalyst regeneration system, a system for effecting heat-up of the reactor and related piping means between vessels which are straight or semicircular conduit means for conveying catalyst particles between the reactor and the regenerator. The steam tubes and the baffle tubes above mentioned are means for restricting gas bubble growth, said baffle tubes being in a specific embodiment, 4 inch nominal diameter tubes hung vertically from support beams. The baffle tubes are open at the top and bottom. They are provided with a plurality of staggered elongated slots in the wall of the baffle tube at spread apart intervals to permit the transfer of catalyst particles and vaporous material into and through the slots in the baffle tubes without substantial flow restriction except to suppress gas bubble growth. A sufficient number of vertical steam tubes and baffle tubes are arranged adjacent to one another in the fluid mass of catalyst particles to restrict bubble growth to an equivalent hydraulic diameter of no more than 24 inches. Equivalent hydraulic diameter will preferably fall within the range of from about 2 to 8 inches and more preferably from about 4 to about 6 inches. For purposes of this invention, the equivalent hydraulic diameter of a reactant bubble is the diameter of a sphere which would provide the same volume as the actual reactant bubble in the catalyst bed.

In one specific embodiment of the apparatus arrangement herein described, which is suitable for production of products enriched in gasoline boiling range hydrocarbons, it is contemplated utilizing a catalyst inventory for the reactor and regenerator arrangement of about 933,000 pounds based on a reactor size, providing a catalyst bed depth of about 40 feet in a 35 foot diameter reactor. It is also contemplated using a catalyst bed depth less than 40 feet, such as 20 or 30 feet, especially when producing olefin-enriched hydrocarbon products. The specific apparatus arrangement and size herein described are designed for processing about 52,640 BPD of crude distilled methanol containing up to about 4% water and producing, under one set of selected operating conditions, about 13,400 BPD of $C_5^+$ gasoline boiling range products plus light olefins, paraffins, isoparaffins and naphthenes as secondary products. Alkylation of olefinic secondary products may be accomplished in separate equipment known in the art in order to further increase production of gasoline boiling range products.

The crystalline zeolites utilized herein are members of a special class of zeolitic materials which exhibit unusual properties. Although these zeolites have unusually low alumina contents, i.e. high silica to alumina mole ratios, they are very active even when the silica to alumina mole ratio exceeds 30. The activity is surprising, since catalytic activity is generally attributed to framework aluminum atoms and/or cations associated with these aluminum atoms. These zeolites retain their crystallinity for long periods in spite of the presence of steam at high temperature which induces irreversible collapse of the framework of other zeolites, e.g. of the X and A type. Furthermore, carbonaceous deposits, when formed, may be removed by burning at higher than usual temperatures to restore activity. These zeolites, used as catalysts, generally have low coke-forming activity and therefore are conducive to long times on stream between regenerations by burning carbonaceous deposits with oxygen-containing gas such as air.

An important characteristic of the crystal structure of this particular class of zeolites is that it provides a selective constrained access to and egress from the intracrystalline free space by virtue of having an effective pore size intermediate between the small pore Linde A and the large pore Linde X, i.e. the pore windows of the structure are of about a size such as would be provided by 10-membered rings of silicon atoms interconnected by oxygen atoms. It is to be understood, of course, that these rings are those formed by the regular disposition of the tetrahedra making up the anionic framework of the crystalline zeolite, the oxygen atoms themselves being bonded to the silicon (or aluminum, etc.) atoms at the centers of the tetrahedra.

The silica to alumina mole ratio referred to may be determined by conventional analysis. This ratio is meant to represent, as closely as possible, the ratio in the rigid anionic framework of the zeolite crystal and to exclude aluminum in the binder or in cationic or other form within the channels. Although zeolites with a silica to alumina ratio of at least 12 are useful, it is preferred in some applications to use zeolites having higher silica/alumina ratios of at least about 30. In addition, zeolites as otherwise characterized herein but which are substantially free of aluminum, i.e. having silica to alumina mole ratios of 1,600 and higher, are found to be useful and even preferable in some instances. Such "high silica" or "highly siliceous" zeolites are intended to be included within this description. Also to be included within this definition are substantially pure silica analogs of the useful zeolites described herein, i.e. those zeolites having no measurable amount of aluminum (silica to alumina mole ratio of infinity) but which otherwise embody the characteristics disclosed herein.

Members of this particular class of zeolites, after activation, acquire an intracrystalline sorption capacity for normal hexane which is greater than that for water, i.e. they exhibit "hydrophobic" properties. This hydrophobic character can be used to advantage in some applications.

The special class of zeolites useful herein have an effective pore size such as to freely sorb normal hexane. In addition, the structure must provide constrained access to larger molecules. It is sometimes possible to judge from a known crystal structure whether such constrained access exists. For example, if the only pore windows in a crystal are formed by 8-membered rings of silicon and aluminum atoms, then access by molecules of larger cross-section than normal hexane is excluded and the zeolite is not of the desired type. Windows of 10-membered rings are preferred, although in some instances excessive puckering of the rings or pore blockage may render these zeolites ineffective.

Although 12-membered rings in theory would not offer sufficient constraint to produce advantageous conversions, it is noted that the puckered 12-ring structure of TMA offretite does show some constrained access. Other 12-ring structures may exist which may be operative for other reasons and, therefore, it is not the present intention to entirely judge the usefulness of a particular zeolite solely from theoretical structural considerations.

Rather than attempt to judge from crystal structure whether or not a zeolite possesses the necessary constrained access to molecules of larger cross-section than normal paraffins, a simple determination of the "Constraint Index" as herein defined may be made by passing continuously a mixture of an equal weight of normal hexane and 3-methylpentane over a sample of zeolite at atmospheric pressure according to the following procedure. A sample of the zeolite, in the form of pellets or extrudate, is crushed to a particle size about that of coarse sand and mounted in a glass tube. Prior to testing, the zeolite is treated with a stream of air at 540° C. for at least 15 minutes. The zeolite is then flushed with helium and the temperature is adjusted between 290° C. and 510° C. to give an overall conversion of between 10% and 60%. The mixture of hydrocarbons is passed at 1 liquid hourly space velocity (i.e., 1 volume of liquid hydrocarbon per volume of zeolite per hour) over the zeolite with a helium dilution to give a helium to (total) hydrocarbon mole ratio of 4:1. After 20 minutes on stream, a sample of the effluent is taken and analyzed, most conveniently by gas chromatography, to determine the fraction remaining unchanged for each of the two hydrocarbons.

While the above experimental procedure will enable one to achieve the desired overall conversion of 10 to 60% for most zeolite samples and represents preferred conditions, it may occasionally be necessary to use somewhat more severe conditions for samples of very low activity, such as those having an exceptionally high silica to alumina mole ratio. In those instances, a temperature of up to about 540° C. and a liquid hourly space velocity of less than 1, such as 0.1 or less, can be employed in order to achieve a minimum total conversion of about 10%.

The "Constraint Index" is calculated as follows:

$$\text{Constraint Index} = \frac{\log_{10}(\text{fraction of hexane remaining})}{\log_{10}(\text{fraction of 3-methylpentane remaining})}$$

The Constraint Index approximates the ratio of the cracking rate constants for the two hydrocarbons. Zeolites suitable for the present invention are those having a Constraint Index of about 1 to 12. Constraint Index (C.I.) values for some typical materials are:

|  | C.I. |
| --- | --- |
| ZSM-4 | 0.5 |
| ZSM-5 | 8.3 |
| ZSM-11 | 8.7 |
| ZSM-12 | 2 |
| ZSM-23 | 9.1 |
| ZSM-35 | 4.5 |
| ZSM-38 | 2 |
| ZSM-48 | 3.4 |
| TMA Offretite | 3.7 |
| Clinoptilolite | 3.4 |
| Beta | 0.6 |
| H—Zeolon (mordenite) | 0.4 |
| REY | 0.4 |
| Amorphous Silica-Alumina | 0.6 |
| Erionite | 38 |

The above-described Constraint Index is an important and even critical definition of those zeolites which are useful in the instant invention. The very nature of this parameter and the recited technique by which it is determined, however, admit of the possibility that a given zeolite can be tested under somewhat different conditions and thereby exhibit different Constraint Indices. Constraint Index seems to vary somewhat with severity of operation (conversion) and the presence or absence of binders. Likewise, other variables such as crystal size of the zeolite, the presence of occluded contaminants, etc., may affect the Constraint Index. Therefore, it will be appreciated that it may be possible to so select test conditions as to establish more than one value in the range of 1 to 12 for the Constraint Index of a particular zeolite. Such a zeolite exhibits the constrained access as herein defined and is to be regarded as having a Constraint Index in the range of 1 to 12. Also contemplated herein as having a Constraint Index in the range of 1 to 12 and therefore within the scope of the defined particular class of highly siliceous zeolites are those zeolites which, when tested under two or more sets of conditions within the above-specified ranges of temperature and conversion, produce a value of the Constraint Index slightly less than 1, e.g. 0.9, or somewhat greater than 12, e.g. 14 or 15, with at least one other value within the range of 1 to 12. Thus, it should be understood that the Constraint Index value as used herein is an inclusive rather than an exclusive value. That is, a crystalline zeolite when identified by any combination of conditions within the testing definition set forth herein as having a Constraint Index in the range of 1 to 12 is intended to be included in the instant zeolite definition whether or not the same identical zeolite, when tested under other of the defined conditions, may give a Constraint Index value outside of the range of 1 to 12.

The particular class of zeolites defined herein is exemplified by ZSM-5, ZSM-11, ZSM-12, ZSM-23, ZSM-35, ZSM-38, ZSM-48 and other similar materials.

ZSM-5 is described in greater detail in U.S. Pat. Nos. 3,702,886, 3,941,871, and Re 29,948. The entire descriptions contained within those patents, particularly the X-ray diffraction pattern of therein disclosed ZSM-5, are incorporated herein by reference.

ZSM-11 is described in U.S. Pat. No. 3,709,979. That description, and in particular the X-ray diffraction pattern of said ZSM-11, is incorporated herein by reference.

ZSM-12 is described in U.S. Pat. No. 3,832,449. That description, and in particular the X-ray diffraction pattern disclosed therein, is incorporated herein by reference.

ZSM-23 is described in U.S. Pat. No. 4,076,842. The entire content thereof, particularly the specification of the X-ray diffraction pattern of the disclosed catalyst, is incorporated herein by reference.

ZSM-35 is described in U.S. Pat. No. 4,016,245. The description of that catalyst, and particularly the X-ray diffraction pattern thereof, is incorporated herein by reference.

ZSM-38 is more particularly described in U.S. Pat. No. 4,046,859. The description of that catalyst, and particularly the specified X-ray diffraction pattern thereof, is incorporated herein by reference.

ZSM-48 is more particularly described in European Patent Application No. 80 300 463, published Sept. 3, 1980 as Publication No. 0 015 132, the entire content of which is incorporated herein by reference.

It is to be understood that by incorporating by reference the foregoing patents to describe examples of specific members of the zeolite class with greater particularity, it is intended that identification of the therein disclosed crystalline zeolites be resolved on the basis of their respective X-ray diffraction patterns. As discussed above, the present invention contemplates utilization of such catalysts wherein the mole ratio of silica to alumina is essentially unbounded. The incorporation of the identified patents should therefore not be construed as limiting the disclosed crystalline zeolites to those having the specific silica/alumina mole ratios discussed therein, it now being known that such zeolites may be substantially aluminum-free and yet, having the same crystal structure as the disclosed materials, may be useful or even preferred in some applications. It is the crystal structure, as identified by the X-ray diffraction "fingerprint", which establishes the identity of the specific crystalline zeolite material.

The specific zeolites described, when prepared in the presence of organic cations, are substantially catalytically inactive, possibly because the intracrystalline free space is occupied by organic cations from the forming solution. They may be activated by heating in an inert atmosphere at 540° C. for 1 hour, for example, followed by base exchange with ammonium salts followed by calcination at 540° C. in air. The presence of organic cations in the forming solution may not be absolutely essential to the formation of this type zeolite; however, the presence of these cations does appear to favor the formation of this special class of zeolite. More generally, it is desirable to activate this type catalyst by base exchange with ammonium salts followed by calcination in air at about 540° C. for from about 15 minutes to about 24 hours.

Natural zeolites may sometimes be converted to zeolite structures of the class herein identified by various activation procedures and other treatments such as base exchange, steaming, alumina extraction and calcination, alone or in combinations. Natural minerals which may be so treated include ferrierite, brewsterite, stilbite, dachiardite, epistilbite, heulandite, and clinoptilolite.

The preferred crystalline zeolites for utilization herein include ZSM-5, ZSM-11, ZSM-12, ZSM-23, ZSM-35, ZSM-38 and ZSM-48 with ZSM-5 being particularly preferred.

In a preferred aspect of this invention, the zeolites hereof are selected as those providing among other things a crystal framework density, in the dry hydrogen form, of not less than about 1.6 grams per cubic centimeter. It has been found that zeolites which satisfy all three of the discussed criteria are most desired for several reasons. When hydrocarbon products or by-products are catalytically formed, for example, such zeolites can maximize the production of gasoline boiling range hydrocarbon products. Therefore, the preferred zeolites useful with respect to this invention are those having a Constraint Index as defined above of about 1 to about 12, a silica to alumina mole ratio of at least about 12 and a dried crystal density of not less than about 1.6 grams per cubic centimeter. The dry density for known structures may be calculated from the number of silicon plus aluminum atoms per 1000 cubic Angstroms, as given, e.g., on page 19 of the article ZEOLITE STRUCTURE by W. M. Meier. This paper, the entire contents of which are incorporated herein by reference, is included in PROCEEDINGS OF THE CONFERENCE ON MOLECULAR SIEVES (London, April 1967), published by the Society of Chemical Industry, London, 1968.

When the crystal structure is unknown, the crystal framework density may be determined by classical pycnometer techniques. For example, it may be determined by immersing the dry hydrogen form of the zeolite in an organic solvent which is not sorbed by the crystal. Or, the crystal density may be determined by mercury porosimetry, since mercury will fill the interstices between crystals but will not penetrate the intracrystalline free space.

It is possible that the unusual sustained activity and stability of this special class of zeolites is associated with its high crystal anionic framework density of not less than about 1.6 grams per cubic centimeter. This high density must necessarily be associated with a relatively small amount of free space within the crystal, which might be expected to result in more stable structures. This free space, however, is important as the locus of catalytic activity.

Crystal framework densities of some typical zeolites, including some which are not within the purview of this invention, are:

|  | Void Volume | Framework Density |
| --- | --- | --- |
| Ferrierite | 0.28 cc/cc | 1.76 g/cc |
| Mordenite | .28 | 1.7 |

-continued

|  | Void Volume | Framework Density |
| --- | --- | --- |
| ZSM-5, -11 | .29 | 1.79 |
| ZSM-12 | — | 1.8 |
| ZSM-23 | — | 2.0 |
| Dachiardite | .32 | 1.72 |
| L | .32 | 1.61 |
| Clinoptilolite | .34 | 1.71 |
| Laumontite | .34 | 1.77 |
| ZSM-4 (Omega) | .38 | 1.65 |
| Heulandite | .39 | 1.69 |
| P | .41 | 1.57 |
| Offretite | .40 | 1.55 |
| Levynite | .40 | 1.54 |
| Erionite | .35 | 1.51 |
| Gmelinite | .44 | 1.46 |
| Chabazite | .47 | 1.45 |
| A | .5 | 1.3 |
| Y | .48 | 1.27 |

When synthesized in the alkali metal form, the zeolite is conveniently converted to the hydrogen form, generally be intermediate formation of the ammonium form as a result of ammonium ion exchange and calcination of the ammonium form to yield the hydrogen form. In addition to the hydrogen form, other forms of the zeolite wherein the original alkali metal has been reduced to less than about 1.5% by weight may be used. Thus, the original alkali metal of the zeolite may be replaced by ion exchange with other suitable metal cations of Groups I through VIII of the Periodic Table, including, by way of example, nickel, copper, zinc, palladium, calcium or rare earth metals.

In practicing the methanol conversion process of the present invention, it is useful and preferred to incorporate the above-described crystalline zeolite with a matrix comprising another material resistant to the temperature and other conditions employed in the process. Such matrix material is useful as a binder and imparts greater resistance to the catalyst for the severe temperature, pressure and reactant feed stream velocity conditions encountered in many conversion processes.

Useful matrix materials include both synthetic and naturally occurring substances, as well as inorganic materials such as clay, silica and/or metal oxides. The latter may be either naturally occurring or in the form of gelatinous precipitates or gels including mixtures of silica and metal oxides. Naturally occurring clays which can be composited with the zeolite include those of the montmorillonite and kaolin families, which families include the sub-bentonites and the kaolins commonly known as Dixie, McNamee-Georgia and Florida clays or others in which the main mineral constituent is halloysite, kaolinite, dickite, nacrite or anauxite. Such clays can be used in the raw state as originally mined or initially subjected to calcination, acid treatment or chemical modification.

In addition to the foregoing materials, the zeolites employed herein may be composited with a porous matrix material, such as alumina, silica-alumina, silica-magnesia, silica-zirconia, silica-thoria, silica-beryllia, and silica-titania, as well as ternary compositions, such as silica-alumina-thoria, silica-alumina-zirconia, silica-alumina-magnesia and silica-magnesia-zirconia. The matrix may be in the form of a cogel. The relative proportions of zeolite component and inorganic oxide gel matrix, on an anhydrous basis, may vary widely, with the zeolite content ranging from between about 1 to about 99% by weight and more usually in the range of about 5 to about 80% by weight of the dry composite.

In the reactor arrangement herein described, the heat of reaction obtained by converting the lower alcohol, e.g. methanol-containing, charge is absorbed by the catalyst and in substantial measure by the steam tubes to produce 600 psig steam. For conversion of the feed to a product enriched in gasoline boiling range material, this arrangement is intended to maintain the temperature within the reaction zone, including within the essentially isothermal dense fluidized catalyst bed and in the "dilute" or more dispersed phase of entrained catalyst above the dense catalyst bed, to within the range of from about 600° F. to 800° F., most preferably about 765° F. In this operating environment, it is contemplated achieving conversion of the methanol-containing feed of greater than 95% and preferably about 99.5% to minimize the loss of difficult to recover methanol in process formed water.

For conversion of methanol-containing feed to olefin-enriched hydrocarbon products which are useful as chemical feedstocks, the reactor can be operated in a manner and under conditions which achieve generally lower conversion values for the charge fed to the reactor in comparison with conversion achieved for production of gasoline range products. Generally conversion values of from about 40% to about 95%, and more preferably from about 50% to 60%, are utilized when olefin-enriched hydrocarbon products are desired. When such generally lower conversion occurs, it becomes economical, and in fact preferred, to recover unreacted methanol and dimethylether from the product effluent and to recycle the methanol and dimethylether so recovered back for introduction into the reactor along with fresh methanol-containing feed. It should be understood that the conversion values, by weight, presented herein are calculated on the basis of total oxygenates in the total reactor feed, including recycle if any. Such reactor feed thus frequently comprises methanol, dimethyl ether, ethanol, butanol, propanol, aldehydes, ketones, other ethers and the like.

One adjustment in reactor operating conditions which can be made to effect lower conversion of the methanol-containing feed for the purpose of promoting production of olefin enriched hydrocarbon products is to generally lower the temperature of the catalyst bed. For olefin-enriched chemical feedstock production from methanol-containing feed, it is desirable to maintain the temperature in the reactor within the range of from about 530° F. to 800° F., more preferably from about 600° F. to 765° F.

Under typical operating conditions suitable for production of gasoline boiling range products, including a pressure restriction of about 32 psig at the bottom of the fluid mass of catalyst and about 25 psig at the bottom of the fluid mass of catalyst and about 25 psig in the reactor dispersed catalyst phase and relying upon a nominal gas velocity of about 2 ft./sec., the density of the fluid mass of catalyst in the lower portion of the reactor is about 27 lbs/cu.ft. However, changes in gas velocity or catalyst density can change the bed density to higher and lower values. That is, when it is desired to change product selectivity to one of high olefin content as opposed to high aromatics yield, the reaction time may be reduced by increasing the gas velocity.

On the other hand, olefin formation can be enhanced by increasing the space velocity, e.g., the weight hourly space velocity (WHSV) or weight of feed per weight of catalyst per hour, which decreases the contact time between the feed and catalyst. Thus olefin production can be increased, for example, by lowering the catalyst bed depth while maintaining the same reactor gas velocity as used for production of gasoline boiling range material. In general, a weight hourly space velocity of from about 0.5 to 15, more preferably 1.0 to 3.0, will be employed for production of gasoline boiling range materials, and a WHSV of from about 1.0 to 5.0 can be used for production of olefin-enriched feedstocks.

It is known that large gas bubbles can form in a fluid catalyst system and particularly large diameter, deep, fluidized catalyst beds even if the gas is first injected into the bed in an atomized condition or as very small gas bubbles. It is believed that, to achieve the desired high conversion of methanol-containing feed, e.g. above 95%, for production of gasoline boiling range material, it is essential to severely restrict gas bubble growth to less than 24 inches, and preferably not to exceed about 8 inches, in equivalent hydraulic diameter. More preferably, the equivalent hydraulic diameter of the reactant bubbles should be restricted to within the range of 4 to 8 inches when charging liquid or vaporized methanol-containing feed for contact with the catalyst at the bottom of the fluid bed of catalyst above a distributor grid. To provide the hydraulic restrictions particularly preferred herein, the steam tubes are located vertically within the reactor, in a plurality of separate flow controlled bundles of tubes which can be shut off or separately removed and replaced as required in the event of any malfunctions. Thus, the steam tubes are vertically hung resembling bayonet type heat exchange tubes attached to separate plenum chambers at the top for adding water and removing high pressure steam respectively. In addition to the vertical steam tubes, a plurality of vertical baffle tubes can be provided therebetween which permit the free upflow of catalyst, reactants and reaction products while maintaining the reactor hydraulics as herein provided.

The baffle tubes and the steam tubes can be arranged uniformly over the reactor cross-section in a particular grid pattern or arrangement compatible with obtaining desired heat transfer, restriction of gas bubble growth and provision for recycling centrifugally separated catalyst by diplegs provided to various bed sections such as a bottom, intermediate and/or upper portion of the most dense fluid mass of catalyst in the reactor zone. It is preferred to discharge all dipleg catalyst adjacent the bottom of the bed. The reactor is provided with eight sets of three stage cyclones, in which arrangement all of the diplegs return separated catalyst to a bottom portion of the fluid bed. In addition, the portion of the vessel housing the cyclones may be larger in diameter than that portion of the vessel housing the most dense fluid bed of catalyst and the heat exchange tubes. Such enlargement by reducing reactant velocity will operate to also reduce catalyst entrainment into the cyclones.

The most dense fluid bed of catalyst in the reactor vessel is supported above a horizontal reactant inlet distributor grid perforated by a multiplicity of small diameter holes, about 11,000, providing relatively uniform dispersal of vaporous and/or liquid methanol-containing feed depending on preheat at the bottom of the fluid bed of catalyst. In one particular arrangement, the small diameter feed inlet holes are about 0.25 inch in diameter. The pressure drop across the grid is sufficiently high to insure uniform distribution of feed gas. It is contemplated providing an open ended catalyst transfer tube extending from beneath the feed inlet distributor grid into the dispersed phase above the more dense fluid bed of catalyst. The top end of this open ended tube may be covered by a spaced apart inverted dish shaped plate to inhibit catalyst particles from falling down into the tube. The bottom end of this catalyst transfer tube extends to a low point of the reactor vessel beneath the grid and is provided with nozzle means for injecting a fluidizing gas for conveying catalyst particles falling through the grid during shutdown and before start-up from beneath the grid into the catalyst system above the grid. Thus it is contemplated fluidizing the mass of catalyst passed to the reactor and in the reactor with an inert gas such as nitrogen or other material suitable for the purpose to clear the chamber in the reactor beneath the grid of catalyst and to fluidize the catalyst bed before injecting the methanol-containing charge under selected reaction conditions.

It will be quite apparent from the discussion herein presented that the arrangement of apparatus and the method of utilizing such apparatus are designed to accomplish dehydration of alcohol in the charge to its corresponding ether and to effect conversion thereof to at least olefins and/or aromatics. It is generally preferred, however, that the operation be performed under conditions restricting the formation of durene. However, formation of some durene (1, 2, 4, 5-tetramethyl benzene) is not fatally restricting to the process. This can be restricted by limiting contact between formed aromatics and methanol charged.

In a reactor system particularly identified and its operation as herein identified, there is a large circulation of catalyst within the dense fluid catalyst bed and within the more dispersed catalyst phase, above the dense bed, as well as between the catalyst phases through the cyclones returning catalyst to the lower portion of the catalyst bed by the cyclone diplegs. It is contemplated circulating from about 4 to 8 million pounds per hour of catalyst in the specifically identified apparatus of this invention; the major portion of the cyclone separated catalyst flows through the diplegs of the first stage cyclones of which there are eight in the specific apparatus embodiment. The circulated catalyst will accumulate carbonaceous deposits thereon of a relatively high order of magnitude, since only a portion of this circulated catalyst is withdrawn for passage to catalyst regeneration for burning a portion of the deposited carbonaceous material in a separate temperature restricted catalyst regeneration zone. In the methanol conversion apparatus arrangement, it is contemplated maintaining a high coke level on internally circulated catalyst to preferentially promote the product of olefins and/or aromatics and isoparaffins. Thus the level of coke-like material (hydrocarbonaceous) retained on the catalyst is generally maintained within the range of 5 to 20% or even 30% by weight. When production of gasoline boiling range products is desired, catalyst coke level is preferably maintained within the range of about 10% to 15% or even 20% by weight. When production of olefin-enriched material is desired, catalyst coke level is preferably maintained within the range of from about 15% to 30% by weight.

FIG. I is a diagrammatic sketch in elevation of the reactor apparatus of this invention comprising an arrangement of heat exchange tubes and baffle tubes positioned in a lower portion of the reactor vessel and spaced vertically above a distributor grid means.

FIG. II is a diagrammatic sketch of a portion of cross-section A—A of FIG. I, showing the relationship between heat exchange tubes, baffle tubes and cyclone diplegs.

FIG. III is a view of a portion of the open end baffle tube showing the arrangement for slotting the tube wall.

Referring now to FIG. I by way of example, a reactor vessel 2 is shown provided with heat exchange tube means 4 and baffle tube means 6. The arrangement of these tube means with respect to one another is more clearly shown by the cross-sectional view and arrangement of FIG. II. Furthermore, it is to be understood that there are several separate heat exchange steam generating tube bundles so that temperature control can be separately exercised over different portions of the fluid catalyst bed. The bottoms of the tubes are spaced above a feed distributor grid 8 approximately 2 feet in a specific arrangement and sufficiently above the grid to be free of jet action by the charged feed through the small diameter holes in the grid. As mentioned above, the holes in the grid are 0.25 inch in diameter, and in one specific arrangement there are approximately 11,000 holes. Provision is made for withdrawing catalyst from above grid 8 as by conduit means 10 provided with flow control valve 12 for passage to catalyst regeneration not shown. Provision is also made for passing the partially regenerated catalyst to the reactor fluid bed of catalyst as by conduit means 14 provided with flow control valve 16. The regenerated cayalyst is charged to the catalyst bed beneath the upper interface and sufficiently below to achieve good mixing in the fluid bed. Since the amount of regenerated catalyst passed to the reactor is small by comparison, the temperature of the regenerated catalyst does not upset the temperature constraints of the reactor operations in a significant amount.

The reactor arrangement of the invention is provided as mentioned above with conduit means 18 such as a riser conduit for removing catalyst from a bottom portion of the vessel beneath grid 8 to an upper portion of the vessel for discharge above the bed upper dense phase interface as shown. Conduit means 21 is provided for charging an inert gas such as nitrogen for use as lift gas for removing catalyst particles by passing a suspension thereof upwardly through riser 18. The top of the riser is capped, for example, by a dish shaped baffle as shown to reduce flow of catalyst down through the riser. Conduit 21 may comprise a vertically moving plug type valve at the bottom inlet which will be closed when charging methanol to the chamber beneath grid 8.

The methanol-containing feed with or without nitrogen or another appropriate diluent, and with or without recycle of unreacted methanol or dimethylether, may be charged through one or more openings 20 and 22 in a bottom extended portion of the reactor. The methanol-containing feed in liquid condition can be sprayed by suitable means into the bed above the grid. The charged methanol-containing feed in vaporous condition enters the vessel by inlet means 20 and 22 in open communication with chamber 24 beneath grid 8. The charged methanol passes through reactant distributor grid 8 and into the bed of catalyst thereabove at a velocity sufficient to form a generally upwardly flowing suspension of reactant and reaction product with the catalyst particles. The suspended catalyst in a concentration generally less than 35 lbs/cu.ft. and about 27 lbs/cu.ft. in a specific arrangement is in random fluid movement in the bed by upflowing gasiform material, with a substantial portion thereof moving generally upward with the gasiform product material into a more dispersed catalyst phase 28 above catalyst bed interface 26.

A plurality of sequentially connected cyclone separator means 30, 32 and 34 provided with diplegs 36, 38 and 40 respectively are positioned in an upper portion of the reactor vessel comprising dispersed catalyst phase 28. In a specific arrangement, there are eight sets of three stage cyclone separating means provided in an upper portion of the reactor vessel. As shown by FIG. II, provision is made for extending the cyclone diplegs into the dense fluid bed of catalyst and preferably to a bottom portion of the fluid bed for discharge in a vertical space between grid 8 and the bottom of tubes 4 and 6 within the bed of about 2 feet. Thus in the reactor arrangement of this invention and the proposed method of utilization for converting methanol to hydrocarbons comprising olefins, aromatics, paraffins and naphthenes, the operation contemplates a high circulation rate of catalyst within the reactor vessel. In a specific example, the reactor catalyst inventory is about 878,500 pounds, and from about 4 to 8 million pounds per hour of catalyst are circulated primarily through the cyclones. In conjunction with this high catalyst circulation operation, it is contemplated maintaining the following specific reactor operating conditions in a specific embodiment wherein gasoline boiling range products are produced:

| Feed to Grid 8 | |
|---|---|
| Methanol, mph | 19,785 |
| Recycle gas, mph | 1,522 |
| Condition below Grid 8 | |
| Temperature, °F. | 350 |
| Pressure, psig | 34.5 |
| Condition above Grid | |
| Temperature, °F. | 765 |
| Pressure, psig | 32.2 |
| Fluidized Catalyst Bed Depth, ft. | 40 |
| Fluidized Catalyst Bed Density, lbs/cu.ft. | 27 |
| Fluidized Bed Pressure Drop, psi | 7.5 |

The product effluent of methanol conversion separated from catalyst particles in the cyclone separating system then passes to a plenum chamber 42 before withdrawal therefrom by one or more opening means 44 and 46. The product effluent recovered by openings 44 and 46 is cooled and separated in means not shown to recover liquid hydrocarbons, gaseous material and formed water comprising some catalyst fines. Since conversion of the methanol-containing feed is at least 95% and preferably at least 99% for production of gasoline boiling range material, the water phase with unreacted methanol is not processed for economic reasons to recover unreacted methanol. The recovered hydrocarbon product comprising olefins and/or aromatics, paraffins and naphthenes is thereafter processed as required to provide a desired gasoline or higher boiling product. In the event the reaction conditions selected produce considerable materials higher boiling than gasoline such as a light fuel oil, the higher boiling material is separated from the gasoline product for further use as desired. Light gaseous hydrocarbon products of the process may be processed as by alkylation, olefination and other known processes to produce gasoline boiling components, LPG, etc. In the embodiment of this invention wherein production of gasoline range materials is to be maximized, it is also contemplated to admix the feed with some of these hydrocarbon gaseous products of the conversion reaction. In order to increase production of gasoline range products, it is particularly advantageous to use ethylene, produced in the reaction and separated in the downstream separation equipment, as the gaseous material recycled and admixed with the feed in conduits 20 and 22 shown in FIG. I.

When the reactor is operated under conditions suitable for producing a product enriched in olefins and therefore suitable for use as chemical feedstocks, feed conversion in a single pass through the reactor can be as low as 40%. In this instance the reactor overhead products generally include significant amounts of unreacted methanol, dimethylether, hydrocarbons consisting of olefins, paraffins, napthenes and aromatics, along with water and minor amounts of related organic acids and other oxygenates. These overhead materials can be processed using conventional refinery equipment into hydrocarbon gases and liquids and a process water stream. The processing streams can also include recovery of the dimethylether and unreacted methanol for recycle back to the reactor for further conversion into hydrocarbon products. As noted at least 40of the total reactor feed, which can comprise fresh methanol, recycle methanol and recycle dimethylether, can be converted to hydrocarbons on a total reactor feed basis.

The total catalyst inventory for the reactor and regenerator (not shown) is about 933,000 pounds based on a 40 foot catalyst bed depth in the reactor. Therefore the regenerator catalyst inventory is about 54,500 pounds in a specific embodiment suitable for methanol conversion to gasoline boiling range products. The catalyst regenerator contemplated for use with the reactor system of this invention can be substantially any arrangement suitable for the purpose and consistent with providing a low temperature regeneration of the catalyst below 1000° F. to effect only partial coke removal by burning. Thus a dense fluid catalyst bed regeneration system may be successfully employed. The density of the regenerator fluid bed of catalyst may be the same as, slightly higher or lower than, the reactor bed density. Generally it will be about 27 lbs/cu.ft. or slightly higher to provide a proper pressure balanced system. In order to restrict the coke burning operation within limits desired, the top of the dense bed is preferably restricted not to exceed a temperature of about 900° F. and the regenerated catalyst outlet temperature preferably should not exceed about 950° F. The pressure within the regenerator is preferably about 29.2 psig at the base of the fluid bed of catalyst in the bottom portion of the regenerator. A catalyst bed depth of about 30 feet is proposed for this specific operation. The incompletely regenerated catalyst particles carrying a high level of coke thereon are recovered from the catalyst regeneration operation not shown and returned to the methanol conversion reactor at a restricted temperature by conduit 14.

Important aspects of the lower alcohol conversion reactor and processes herein described are manifold, since they include (1) restricting the exothermic temperature generated within relatively narrow limits; (2) restricting the reactant vapor bubble growth within particular limits; (3) maintaining a catalyst condition particularly promoting the formation of olefins and/or aromatics, paraffins, and naphthenes depending on feed composition comprising methanol and depending on whether gasoline boiling range or olefin-enriched chemical feedstock products are desired; (4) maintaining a reaction condition promoting greater than 95% conversion of the methanol-containing charge to more desirable products when gasoline boiling range products are desired and from about 40% to about 95% conversion of the methanol-containing reactor charge when olefin-enriched chemical feedstocks are desired; and (5) maintaining a catalyst circulation system within operating restrictions above identified and particularly promoting the conversion of methanol-containing feed to either olefinic and/or aromatic gasoline boiling components or to olefin-enriched hydrocarbons useful as chemical feedstocks.

One of the more important aspects above identified is concerned with the removal of exothermic heat and restricting the vaporous reactant hydraulic diameter. FIG. II identifies a cross-sectional view A—A of the apparatus of FIG. I having a particular bearing on these important aspects. That is, FIG. II shows the systematic relationship between vertically positioned steam tubes 50 shown as black dots with baffle tubes 52 to achieve the desired heat exchange and maintain a desired reactant hydraulic diameter or gas bubble growth restriction. FIG. II also shows the arrangement of cyclone standpipes 54, 56, 58, 60, 62, 64, 66, 68 and 70 provided for accomplishing the catalyst circulation desired. In each quarter section of the reactor cross-sectional area, there are at least six standpipes for returning cyclone separated catalyst to the fluid bed of catalyst. In addition, the 4 inch diameter tubes, comprising steam tubes 30 and baffle tubes, are spaced on a grid pattern of 6 inch square or pitch which are grouped into 36 inch square bundles, each typically containing 4 steam tubes and 32 baffle tubes. In the reactor design of this invention, there are 352 steam tubes and 3,192 baffle tubes. The hydraulic diameter of each 36 inch square tube bundle is about 5.3 inches when using 4.5 in O.D. tubes in a specific arrangement. However, the hydraulic diameter of the reactor is about 6 inches.

The baffle tubes 52 used in the apparatus are particularly shown in partial view in FIG. III. These baffle tubes 52 confined with the dense fluid bed of catalyst as herein provided are open ended tubes, about 4 inches in diameter or 4.5 inch O.D. tubes, and slotted in the wall as shown to provide approximately 2×4 inch slots to permit ingress and egress of catalyst particles and vaporous material within the bubble breaking constraints of this invention. For a baffle tube of 4 inch diameter, the slots are generally round on each end and arranged in a pattern in the tube wall throughout a major portion of its length.

Baffle tubes such as those shown are useful in maintaining the requisite restrictions on reactant equivalent hydraulic diameter. Baffles are generally not required in the reaction zone for the production of olefin-enriched chemical feedstock products since the conversion requirements for this mode of operation are lower than for production of gasoline products, and conversion can be maintained by appropriate adjustment of space velocity, reactor temperature and catalyst coke level. Such baffles may, however, be utilized to increase feed conversion for production of olefin-enriched products at higher space velocities by constraining bubble growth and maximizing catalyst particle/vapor contact.

FIGS. II and III are believed to be generally self-explanatory when considered in the light of the discussion above and minor deviations therefrom are considered to be within the scope of the invention.

Having thus generally described the method and apparatus of this invention and described specific examples in support thereof, it is to be understood that no undue restrictions are to be imposed by reasons thereof except as defined by the following claims.

What is claimed is:

1. A method for converting reactant materials selected from the group consisting of lower alcohols, either derivatives thereof, oxygenates of synthesis gas and any one or a combination thereof, which process comprises:
    passing the reactant material in vaporous, liquid or mixed liquid-vapor condition upwardly through a fluid bed of zeolite catalyst particles, said zeolite characterized by a silica/alumina ratio of at least 12, a pore opening of at least 5 Angstroms and a Constraint Index within the range of about 1 to 12, at a temperature constrained within the range of about 530° F. to about 800° F. under pressure and space velocity conditions selected to achieve from about 40% to about 95% conversion of the reactant materials passed to the bed to olefin-enriched hydrocarbon products, said temperature constrained limits achieved at least in part by a plurality of heat exchange tubes immersed in a fluid bed of said catalyst and providing high pressure steam therein as a result of said heat exchange, said reactant material restricted in gasified bubble growth to less than 24 inch equivalent hydraulic diameter during contact with said bed of fluid catalyst particles by said heat exchange tubes or by a plurality of vertical open ended baffle tubes slotted in the wall thereof for flow of catalyst and gasiform reactant material therethrough adjacently positioned in combination with said heat exchange tubes, said reactant conversion exotherm further constrained by maintaining from 5% to 30% by weight of coke-like material on the zeolite catalyst in the reaction zone;
    maintaining a high rate of catalyst circulation from a dispersed catalyst phase above said fluid catalyst bed to a bottom portion of said bed following separation of reaction product from said catalyst passing into said dispersed phase; and
    recovering olefin-enriched hydrocarbon products of said conversion operation.

2. The method of claim 1 wherein the reactant material comprises methanol charged in a vaporous condition to the fluid bed of catalyst.

3. The method of claim 2 wherein pressure and space velocity conditions are selected to achieve from about 50% to 60% conversion of the reactant material passed to the catalyst bed; wherein unconverted methanol and dimethylether are separated from the recovered products of said conversion operation and wherein said unconverted methanol and dimethylether are recycled to the catalyst bed by combining said unconverted methanol and dimethylether with the reactant material charged to the catalyst bed.

4. The method of claim 1 wherein the reactants are passed to the fluid bed of catalyst maintained at a temperature of from about 600° F. to 765° F.

5. The method of claim 1 wherein the coke material retained on the catalyst is from about 15% to 30% by weight percent.

6. The method of claim 1 wherein a small portion of the reaction zone catalyst inventory is passed to a temperature restricted catalyst regeneration operation to achieve only partial removal of coke-like material thereafter returned to the reaction zone at a relatively low temperature below 1000° F.

7. The method of claim 1 wherein the gasified bubble growth is restricted between about 8 inch and 24 inch equivalent hydraulic diameter.

8. The method of claim 3 wherein weight hourly space velocity is maintained within the range of from about 1.0 to 5.0, reaction temperature is maintained within the range of from about 600° F. to 765° F. and catalyst coke level is maintained within the range of from about 15% to 30% weight.

9. The method of claim 1 wherein space velocity, catalyst bed temperature and catalyst coke level are maintained such that at least about 40% conversion of the reactant material is realized without utilization of baffle tubes in the catalyst bed.

* * * * *

UNITED STATES PATENT AND TRADEMARK OFFICE
CERTIFICATE OF CORRECTION

PATENT NO. : 4,423,274

DATED : December 27, 1983

INVENTOR(S) : NICHOLAS DAVIDUK and JAMES H. HADDAD

It is certified that error appears in the above-identified patent and that said Letters Patent is hereby corrected as shown below:

Column 8, line 22: "be" should be --by--

Column 9, lines 55 & 56: delete "at the bottom of the fluid mass of catalyst and about 25 psig"

Column 14, line 24: "40of" should be --40% of--

Signed and Sealed this

Nineteenth Day of June 1984

[SEAL]

Attest:

Attesting Officer

GERALD J. MOSSINGHOFF

Commissioner of Patents and Trademarks